(12) United States Patent
Ghosh et al.

(10) Patent No.: US 9,409,143 B2
(45) Date of Patent: Aug. 9, 2016

(54) PROCESS FOR CONDUCTING ORGANIC REACTIONS IN A STANDALONE AND AFFORDABLE LABORATORY SCALE SOLAR PHOTO THERMOCHEMICAL REACTOR

(71) Applicant: Council of Scientific & Industrial Research, New Delhi (IN)

(72) Inventors: Pushpito Kumar Ghosh, Gujrat (IN); Supratim Chakraborty, Gujrat (IN); Milan Dinda, Gujrat (IN); Subarna Maiti, Gujrat (IN); Chitrangi Bankimbhai Bhatt, Gujrat (IN); Jitendra Narsinhbhai Bharadia, Gujrat (IN); Pankaj Arvindbhai Patel, Gujrat (IN); Pratap Shashikant Bapat, Gujrat (IN)

(73) Assignee: COUNCIL OF SCIENTIFIC & INDUSTRIAL RESEARCH, New Delhi (IN)

(*) Notice: Subject to any disclaimer, the term of this patent is extended or adjusted under 35 U.S.C. 154(b) by 0 days.

(21) Appl. No.: 14/413,656

(22) PCT Filed: Jul. 9, 2013

(86) PCT No.: PCT/IB2013/055634
§ 371 (c)(1),
(2) Date: Jan. 8, 2015

(87) PCT Pub. No.: WO2014/009882
PCT Pub. Date: Jan. 16, 2014

(65) Prior Publication Data
US 2015/0196891 A1 Jul. 16, 2015

(30) Foreign Application Priority Data
Jul. 9, 2012 (IN) .......................... 2117/DEL/2012

(51) Int. Cl.
*B01J 19/18* (2006.01)
*B01J 19/12* (2006.01)
(Continued)

(52) U.S. Cl.
CPC ............... *B01J 19/18* (2013.01); *B01J 19/127* (2013.01); *C07B 39/00* (2013.01); *C07C 17/013* (2013.01);
(Continued)

(58) Field of Classification Search
CPC ....... B01J 19/123; B01J 19/127; C02F 1/325; C07C 17/04; C07C 17/013
See application file for complete search history.

(56) References Cited

U.S. PATENT DOCUMENTS

2010/0139648 A1* 6/2010 Bourke .................. F24J 2/0023
126/681

FOREIGN PATENT DOCUMENTS

WO WO 2012/156768 A1 11/2012

OTHER PUBLICATIONS

Dinda, et al. 2012 "Clean synthesis of crystalline p-nitrobenzyl bromide from p-nitrotoluene with zero organic discharge" *RSC Advances* 2(16); 6645-6649.
(Continued)

*Primary Examiner* — Yate K Cutliff
(74) *Attorney, Agent, or Firm* — Knobbe, Martens, Olson & Bear, LLP

(57) ABSTRACT

A process conducts organic reactions in a standalone laboratory scale solar photo thermo chemical reactor. For organic reactions require elevated temperature, light and mechanical agitation, all three energy forms can be simultaneously derived from solar radiation. Organic synthesis, such as bromination of toluene derivatives (benzylic bromination), bromination of cyclic acyclic hydrocarbon and oxidative cyclization of N-phenylethyl benzamide through bromination were successfully conducted in such reactors.

12 Claims, 5 Drawing Sheets

(51) Int. Cl.
  *C07C 201/12* (2006.01)
  *C07B 39/00* (2006.01)
  *C07C 17/10* (2006.01)
  *C07C 17/14* (2006.01)
  *F24J 2/07* (2006.01)
  *H02S 10/40* (2014.01)
  *H02S 40/22* (2014.01)
  *C07C 17/013* (2006.01)
  *C07C 17/04* (2006.01)
  *C07D 263/32* (2006.01)

(52) U.S. Cl.
  CPC ............... *C07C 17/04* (2013.01); *C07C 17/10* (2013.01); *C07C 17/14* (2013.01); *C07C 201/12* (2013.01); *C07D 263/32* (2013.01); *F24J 2/07* (2013.01); *H02S 10/40* (2014.12); *H02S 40/22* (2014.12); *B01J 2219/00051* (2013.01); *C07C 2101/18* (2013.01); *C07C 2102/42* (2013.01); *Y02E 10/41* (2013.01); *Y02E 10/52* (2013.01)

(56) References Cited

OTHER PUBLICATIONS

Dinda, et al. 2013 "Solar photothermochemical reaction and supercritical $CO_2$ work up for a fully green process of preparation of pure p-nitrobenzyl bromide" *Environmental Science & Technology* 47; 10535-10540.

Maiti, et al. 2011 "Performance evaluation of a small scale indirect solar dryer with static reflectors during non-summer months in the Saurashtra region of Western India" *Solar Energy* 85(11); 2686-2696.

Mumba, et al. 1996 "Design and development of a solar grain dryer incorporating photovoltaic powered air circulation" *Energy Conversaion and Management* 37(5); 615-621.

Solanki, et al. 2008 "Enhanced heat dissipation of V-trough PV modules for better performance" *Solar Energy Materials and Solar Cells* 92(12); 1634-1638.

Vivar, et al. 2010 "A concept for a hybrid solar water purification and photovoltaic system" *Solar Energy Materials and Solar Cells* 94(10); 1772-1782.

\* cited by examiner

PROCESS FOR CONDUCTING ORGANIC REACTIONS IN A STANDALONE AND AFFORDABLE LABORATORY SCALE SOLAR PHOTO THERMOCHEMICAL REACTOR

FIELD OF THE INVENTION

The present invention relates to a process for carrying out organic reaction in a laboratory scale device which can be utilized to drive organic reactions which require light, heat and agitation all of which are provided through solar energy.

BACKGROUND AND PRIOR ART OF THE INVENTION

Reference may be made to the article "Insight over view, Alternative energy technologies" published in Nature 414, (2001), 332-337 by M. S. Dresselhaus & I. L. Thomas, which describes "Fossil fuels currently supply most of the world's energy needs, and however unacceptable their long-term consequences, the supplies are likely to remain adequate for the next few generations. Scientists and policy makers must make use of this period of grace to assess alternative sources of energy and determine what is scientifically possible, environmentally acceptable and technologically promising."

Reference may be made to the article "Evaluation of photo contribution to a chemical reaction using concentrated solar energy" published in Solar Energy 44 (1990) 37-42, by W. E. Wentworth et. al, which describes highly concentrated simulated solar energy can be used directly as the energy source to carry out the reaction of 2-propanol to propene and acetone. A focused beam from a 1000 watt xenon lamp is used to simulate concentrated solar energy. The reaction is run with uv-visible cutoff filters which successively remove portions of the uv-visible radiation from the xenon lamp. However the results which demonstrate the simulated solar energy using 1000 w xenon lamp, is not exactly solar radiation and describes only light effect.

Reference may be made to a paper by Stefano Protti et al. entitled "The sunny side of chemistry: green synthesis by solar light", published in Photochemical & Photobiological Sciences, 2009, 8, 1499-1516, the authors report that in many cases the solar radiation could be successfully used in place of toxic or expensive chemical reagents to overcome the activation energy in organic synthesis. However the focus is on light driven reactions and not a combination of light and heat-driven reactions.

Reference may be made to a paper by V. Murugesan et al. entitled "Solar photocatalytic degradation of azo dye comparison of photocatalytic efficiency of ZnO and $TiO_2$", published in Solar Energy Materials & Solar Cells 77 (2003) 65-82 the authors have investigated the photocatalytic activity of commercial $TiO_2$. However the focus is on photo assisted reaction and comparisons with other photo assisted reactions and not a combination of light and heat-driven reactions.

Reference may be made to a paper by Jaime A. Valderrama et al. entitled "The solar-chemical photo-Friedel-Crafts heteroacylation of 1,4-quinones", published in Tetrahedron Letters 52 (2011) 609-6011, the authors report the investigation of photochemical reactions between 1,4-benzo- and 1,4-naphthoquinone and several heteroaromatic carbaldehydes under solar irradiation conditions. However this reaction also focuses on light only not a combination of light and heat-driven reactions.

Reference may be made to the article "Visible light induced 'on water' benzylic bromination with N-bromosuccinimide" published in Tetrahedron Letters 47 (2006) 1097-1099, by Ajda Podgorsek et. al, which describes benzylic bromination of various 4-substituted toluenes (Me, tert-Bu, COOEt and COMe) conducted with NBS in pure water and with a 40 W incandescent light-bulb as an initiator of the radical chain process. However the time taken for most of the reactions is excessively long.

Reference may be made to a paper entitled "Clean synthesis of crystalline p-nitrobenzyl bromide from p-nitrotoluene with zero organic discharge" heat (to raise the reaction temperature to 70-80° C.) and light was utilised in tandem in a fast and selective benzylic bromination reaction (Dinda et. al., RSC Adv., 2 (2012) 6645-6647. However this work utilises conventional energy sources and does not report standalone bromination with solar energy in aqueous medium.

It occurred to us while conducting the above studies that if a solar device can be made available which can provide heat to achieve a controlled temperature in the range of 50-100° C., light in adequate amount, and with provision for agitation with a magnetic stirrer typically preferred by synthetic chemists, then the device can be utilized to carry out such reactions in a "greener" manner which is important for students and researchers to learn in the context of sustainable development besides its wider relevance.

OBJECTS OF THE INVENTION

The object of the present invention relates to a process for carrying out organic reaction in a laboratory scale device which can be utilized to drive organic reactions which require light, heat and agitation all of which are provided through solar energy.

Another object of the present invention is to promote popularization of solar energy use in chemical reactions by making such a device available to colleges and research laboratories at affordable cost.

Another object of the present invention is to promote such objects without compromising on the speed and selectivity of the reactions and the ease of use.

Another object is to design a compact and easy-to-maintain unit.

Another object of the present invention is draw inspiration from V-trough configuration to achieve reaction temperature in the range of 50-100° C.

Another object of the present invention is to utilize a solar-powered fan to control the temperature of the unit and consequently the reaction temperature.

Another object of the present invention is to drive a magnetic stirrer with solar energy Another object of the present invention is to utilise an optically transparent or opaque reactor depending on the need for light or otherwise.

Another object is to raise the photon flux over ambient to accelerate the reactions facilitated by light.

Another object of the present invention is to demonstrate the invention through benzylic bromination reactions promoted by a combination of heat, light and agitation.

Another object of the present invention is to demonstrate the invention through other bromination reactions promoted by a combination of heat, light and agitation.

Another object of the present invention is to conduct the benzylic reactions under solvent-free conditions for complete greening of the process.

SUMMARY OF THE INVENTION

Figure 1:
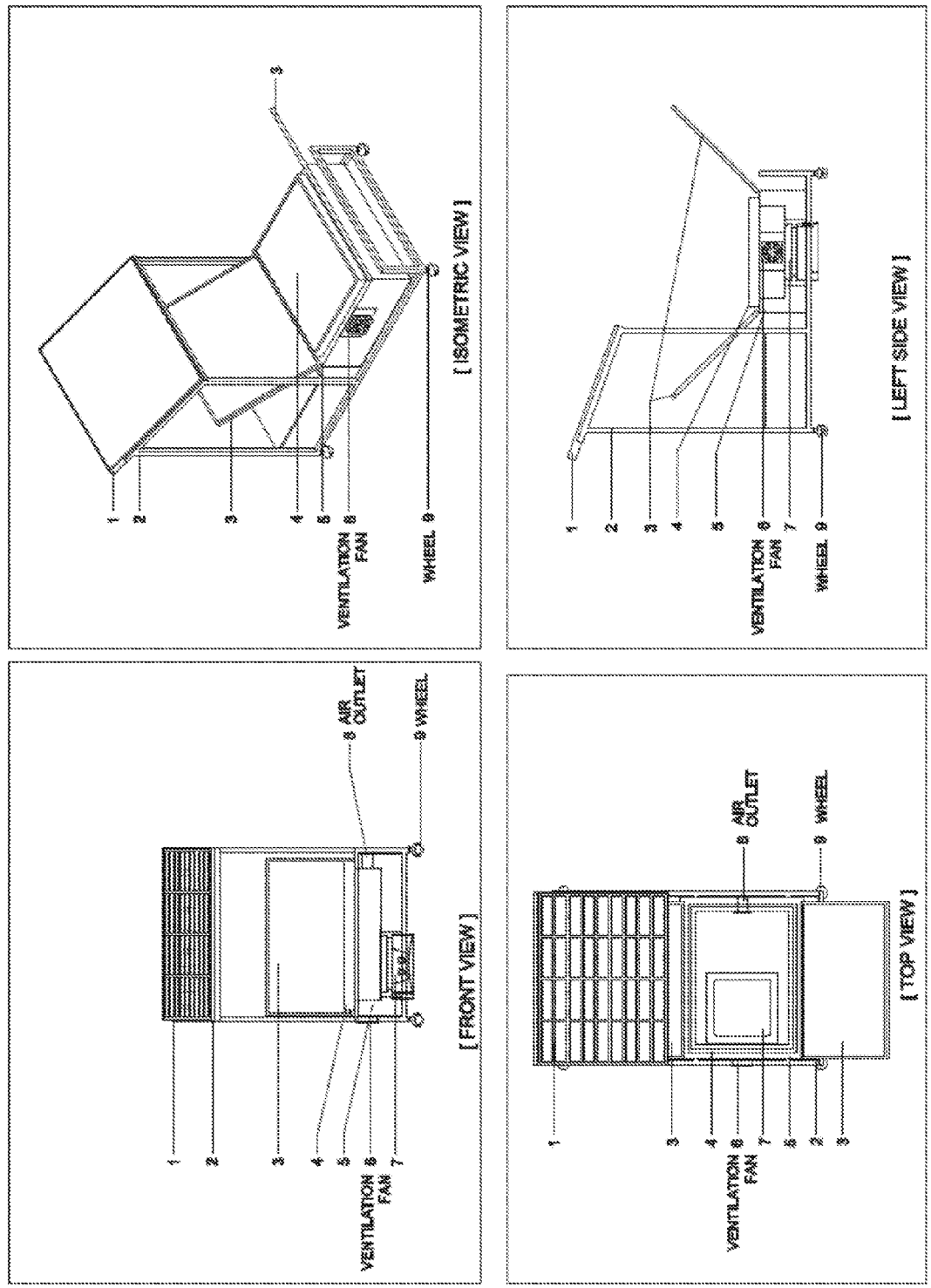
FIG. 1 represents front view, isometric view, top view and side view of solar photo thermo chemical reactor 1 (SPTR-1).
Figure 2:
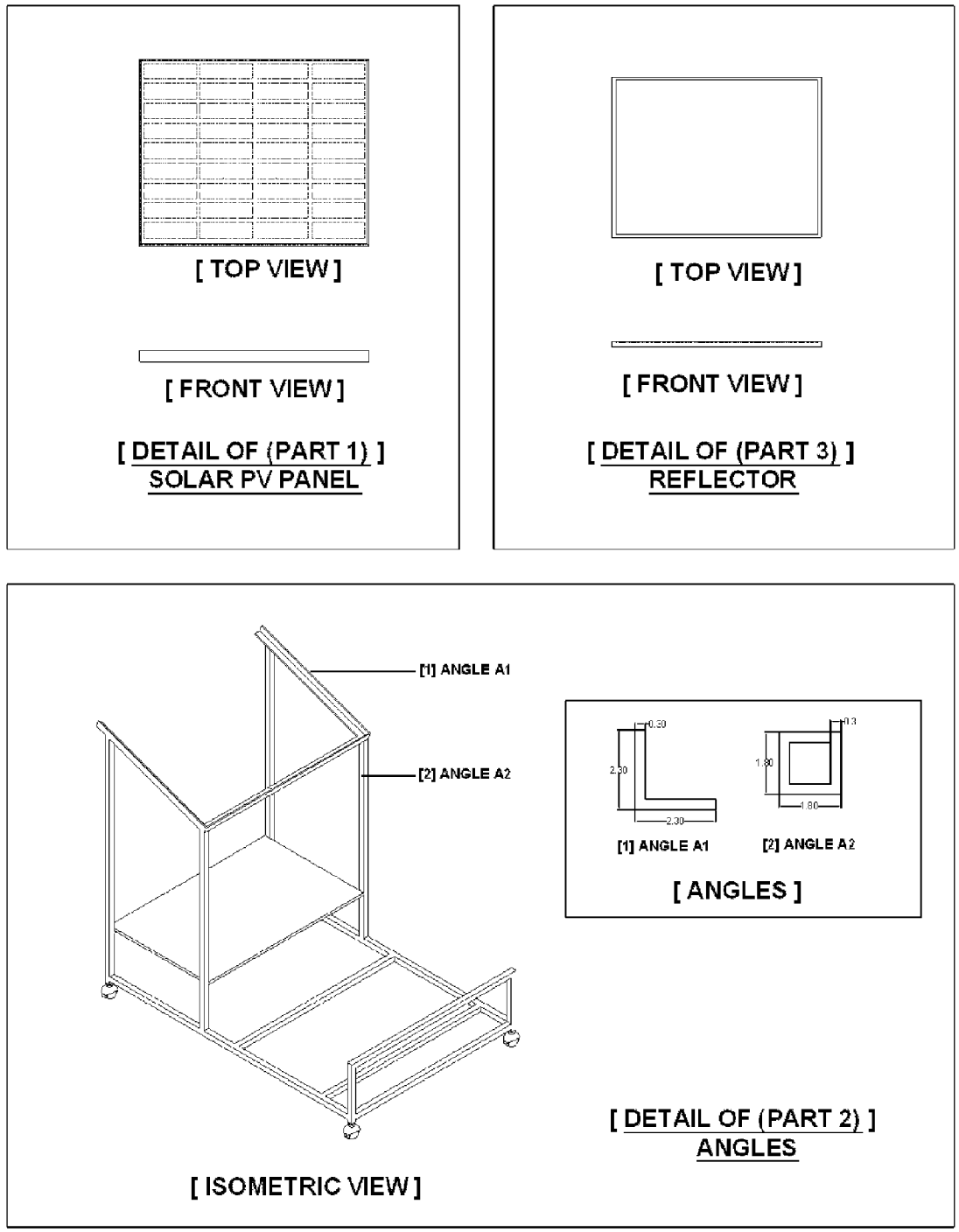
FIG. 2 represents the solar PV panel, reflectors and angle assembly of solar photo thermo chemical reactor 1 (SPTR-1).
Figure 3:
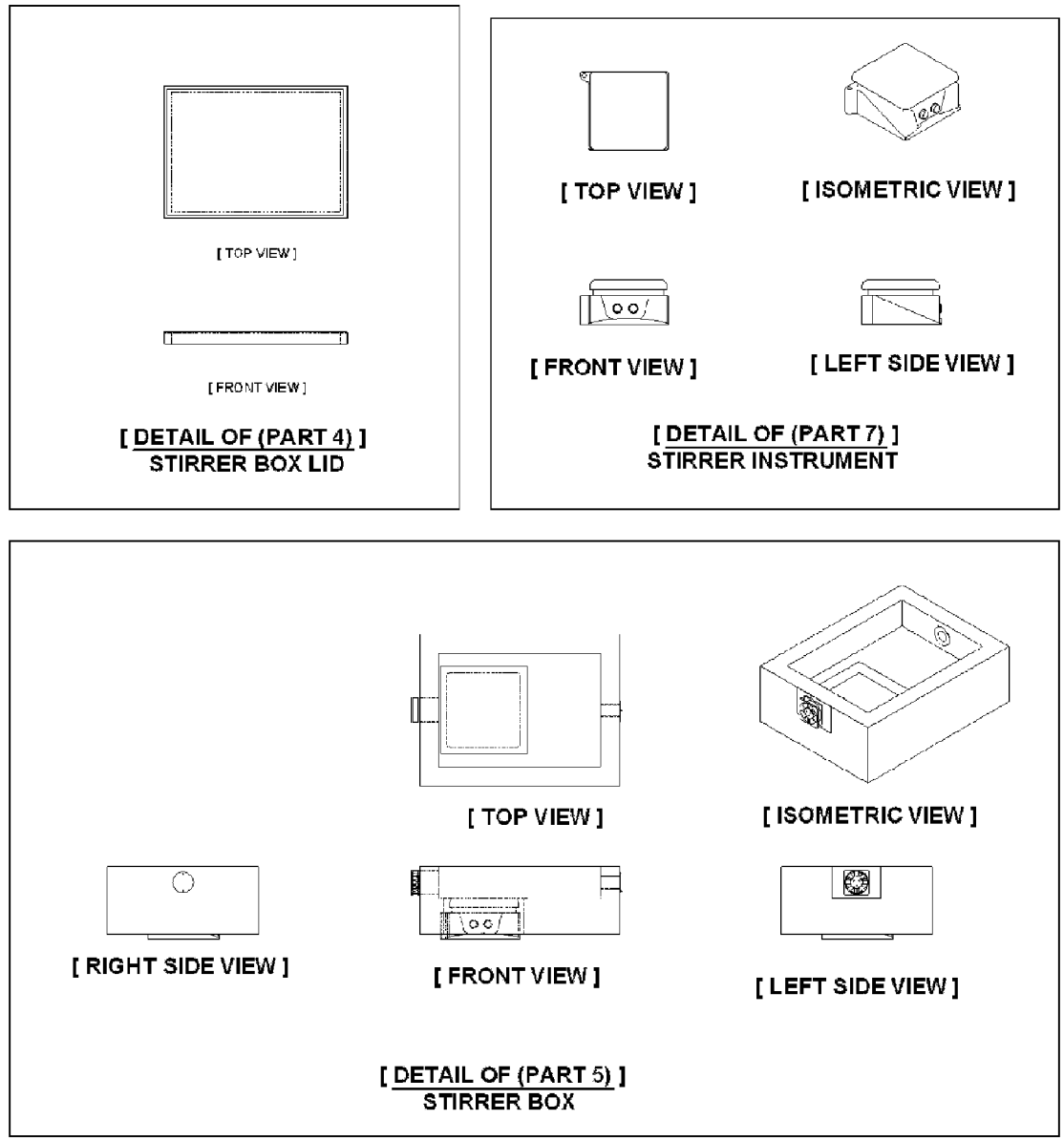
FIG. 3 represents the stirrer assembly and the black colored box with fan of solar photo thermo chemical reactor 1 (SPTR-1).

Accordingly the present invention relates to a process for carrying out organic reaction in a laboratory scale device which can be utilized to drive organic reactions which require light, heat and agitation all of which are provided through solar energy.

In an embodiment of the present invention, scale solar photo thermo chemical reactor comprising a solar Photovoltaic (PV) panel (01) attached to an angle assembly (02) having plurality of V-trough reflectors on the north-south edges (03), over a cooker type black painted box (05) having a lid assembly (04), and Photovoltaic (PV) operated dc fan on one side in the said box (06), and an air outlet for controlling temperature on the other side (08), and also having a PV operated magnetic stirrer at the base of the box (07), and wheels to enable mobility of the entire unit (09).

In yet another embodiment of the present invention, temperatures inside the box in SPTR-1 were measured with RTDs (Resistance temperature detectors), wind speed and ambient temperature were measured using thermo-anemometer and solar intensity during the reaction period was measured using an Eppley PSP pyranometer.

In yet another embodiment of the present invention, 1.5-2.0 times concentration of the solar radiation incident on the reactor SPTR-1 was achieved helping thereby raise the photon flux and reaction temperature.

In yet another embodiment of the present invention, maximum temperature obtained in SPTR-1 on a typical sunny day was 105° C.

In yet another embodiment of the present invention, PV operated dc fan regulate the reaction temperature in the range 50° C. in SPTR-1.

In yet another embodiment of the present invention, said reactions are carried out upto 100 g scale in SPTR-1.

In yet another embodiment of the present invention, said reactor SPTR-1 is useful for bromination at $sp^3$ carbon.

In yet another embodiment of the present invention eight benzylic bromination reactions, six bromination reaction of linear and cyclic aliphatic hydrocarbon and four photo-thermal assisted oxidative cyclization of N-phenylethayl benzamides to 4-bromo 2,5 substituted oxazoles were conducted in SPTR-1.

In yet another embodiment of the present invention solar radiation was incident from the top of the reactor.

In yet another embodiment of the present invention use of the PV operated dc fan regulated the reaction temperature in the range 50-70° C.

In yet another embodiment of the present invention temperature regulation prevented hydrolysis of bromo derivatives to the corresponding alcohols.

In yet another embodiment of the present invention solar photo thermo chemical reactor accommodated up to 500 mL capacity of round bottom flask and may be used for carrying out photo-thermochemical reactions at up to 250 g scale.

In yet another embodiment of the present invention bromination at $sp^3$ carbon was demonstrated to occur speedily with high selectivity.

In yet another embodiment of the present invention, a system for carrying out organic reactions comprising a solar photo thermo chemical reactor (SPTR-1) for simultaneously deriving solar radiations for elevated temperature, light and mechanical agitation.

DETAILED DESCRIPTION OF THE INVENTION

Solar Photo Thermochemical Reactor 1 (SPTR1)

The solar photo-thermochemical reactor 1 (SPTR 1) was fabricated to carry out the reaction which needed thermal energy as well as photon. The basic unit was similar in design to V-trough solar cookers and was specially fitted with a PV panel which operated the in-built magnetic stirrer and fan for temperature regulation.

A rectangular box (0.50 m×0.34 m×0.10 m) made of wood was coated with matt black paint on the inner side. A magnetic stirrer was positioned in the box in such a way that uniform stirring could be insured. A 0.002 m thick detachable transparent commercial glass fixed to a teakwood frame was placed as cover over the box over a rubber gasket strip. The cover could be removed easily for cleaning purposes. The glass cover had a hole on its surface, from which the neck of the flask stuck out to enable addition of chemicals and drawing of samples. Two glass reflectors of 0.58 m×0.44 m were positioned in a V-trough alignment on the two sides of the box in North-South direction. The angle of the reflectors could be adjusted to maximize solar radiation on the glass cover. A 20 watt PV module was positioned on top of the North side reflector in foldable manner. A 12 V, 0.21 A dc fan (Eiffel make) was fitted onto one of the walls of the box while a 0.04 m diameter opening with a flap was kept on the opposite wall to vent out excess trapped heat and thereby control the reaction temperature. The magnetic stirrer and fan were both operated with the same PV panel. The temperatures inside the box were measured with RTDs (Resistance temperature detectors). The wind speed and ambient temperature were measured using a thermo-anemometer (Metershack, CEM DT-618B) having 0-5 $ms^{-1}$ range and 0.01 $ms^{-1}$ reading accuracy. The solar intensity during the reaction period was measured using an Eppley PSP pyranometer (sensitivity=9.3 $\mu V W^{-1} m^2$).

The experiments were carried out in Bhavnagar (21.77° N, 72.15° E), Gujarat, Western India. The reactions can be successfully carried out for 250-260 days in a year in any geographical location having abundant sunlight. The minimum solar radiation required for the reactions to be conducted in these reactors is 700 $wattm^{-2}$.

The main inventive steps are the following:
1. Realisation that solar radiation is a source of both heat and light and can be utilized to drive reactions which require such inputs and, additionally, agitation.
2. Realisation that although many may want to practice such solar-driven reactions, particularly towards demonstration of green processes, they are unable to do so for want of a device.

3. Realisation that although one can, in principle, leave reactions out in the open to get bathed in sunshine, this is subject to the vagaries of nature and, besides, may not lead to sufficiently high temperatures and light flux required to conduct reactions speedily.
4. Recognising that a solar cooker type of design may be a better alternative in view of the confined conditions and illumination from the top instead of from the bottom which would enable use of a magnetic stirrer.
5. Fabricating thereafter a device fitted with North-South reflectors with slots for seasonal tracking which yielded a maximum temperature of 110° C. within the unit under peak summer conditions;
6. Finding out in the course of experimentation that there can be excessive rise of temperature and thereafter using a dc-powered fan to control temperature over a narrow range within the device; additionally, having the provision to vary the temperature in the range of 50-100° C.
7. Making provision for a magnetic stirrer inside the device and controlling the stirring speed from the outside.
8. Using a 20 W PV panel to power the fan and the stirrer.
9. Fitting the PV panel suitably into one of the reflectors with the help of hinges to make a compact foldable device.
10. Having a detachable glass cover with one or more holes through which the neck of the round bottom flask used for reaction can stick out so that substrate, reagent, solvent, etc. can be introduced besides having provision for temperature and other sensors and reflux/distillation assembly.
11. Additionally, the detachable glass cover allows for easy maintenance of the device.
12. Realisation that control of temperature is needed to avoid overheating and hence incorporating a dc powered fan at one side of the box and keeping a air passage at the other side.
15. Demonstrating the utility of the device through benzylic bromination which is speeded up by heat and light in the absence of chemical initiators; further, attaining nearly quantitative yields with respect to reagent in some cases within short reaction times.
16. Additionally, conducting the reaction in the greenest manner by avoiding organic solvents.

EXAMPLES

The following examples are given by way of illustration and therefore should not be construed to limit the scope of the present invention.

Example 1

Maximum Temperature Attainable in SPTR 1

Figure 4:
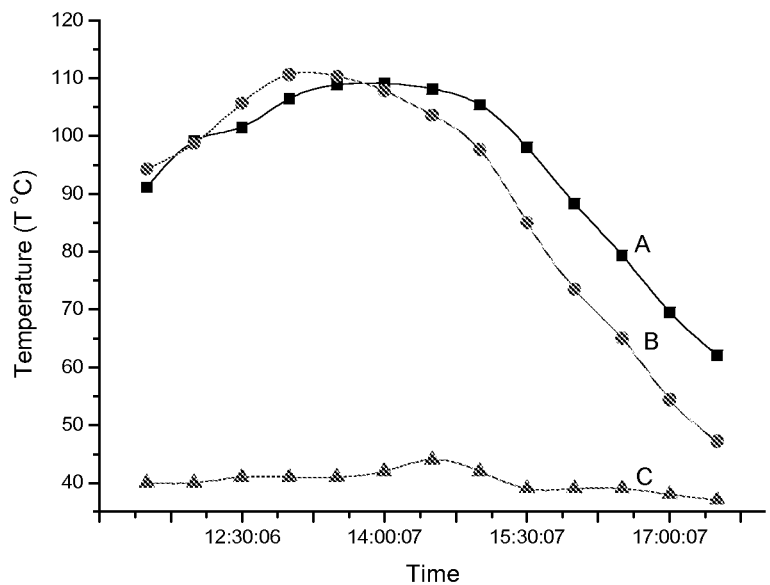
FIG. 4 represents temperature profile graph of glycerol placed in a round bottom flask in SPTR1 (without operation of fan) (A), temperature profile inside the SPTR1, also without the fan (B) and at the ambient temperature (C).

Glycerol was taken in the RB flask and placed in the unit of SPTR1 without operation of the fan and stirrer. The table below lists the interior temperature and glycerol temperature for different ambient conditions 30.05.2012. It can be seen that a maximum temperature of ca. 110° C. could be attained. FIG. 4 represents a temperature profile graph of the glycerol placed in the round bottom flask in SPTR1 (without operation of fan) (A), temperature profile inside the SPTR1 (also without the fan) (B) and at the ambient temperature (C), obtained from Table 1.

TABLE 1

Temperature profile inside the SPTR1 and inside the RBF

| Time | Temp of glycerol placed inside the rb flask | Temp of the interior of the device | Ambient temp | wind speed, m/s | solar intensity, watt/m2 |
|---|---|---|---|---|---|
| 10:30:02 | 73.9 | 81.2 | 39 | 0.6 | 946.2 |
| 11:00:02 | 82.9 | 86.1 | | | |
| 11:30:02 | 91.1 | 94.3 | 40 | 0.9 | 1000 |
| 12:00:02 | 99.1 | 98.7 | | | |
| 12:30:06 | 101.5 | 105.7 | 41 | 1 | 1064.5 |
| 13:00:07 | 106.4 | 110.6 | | | |
| 13:30:07 | 108.8 | 110.3 | 41 | 1.6 | 817.2 |
| 14:00:07 | 109.1 | 107.8 | | | |
| 14:30:07 | 108.1 | 103.6 | 44 | 1.6 | 903.2 |
| 15:00:07 | 105.4 | 97.6 | | | |
| 15:30:07 | 98 | 85 | 39 | 0.9 | 741.9 |
| 16:00:07 | 88.3 | 73.5 | | | |
| 16:30:07 | 79.3 | 65 | 39 | 0.6 | 591.3 |
| 17:00:07 | 69.5 | 54.4 | | | |
| 17:30:07 | 62.1 | 47.2 | 37 | 1.1 | 279.5 |

Example 2

Temperature Control in SPTR1

Figure 5:
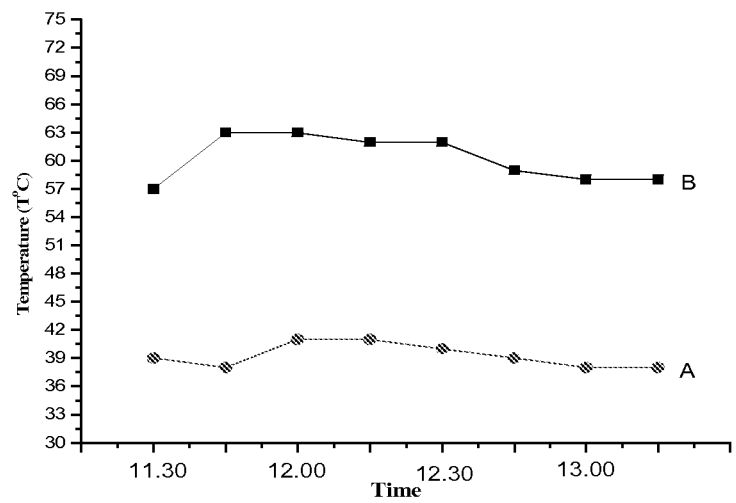
FIG. 5 represents the temperature profile graph with operation of fan in SPTR-1 (B) and at the ambient temperature (A).

In the similar way of Example 1, temperature in the range of 55-70° C. could be maintained with the operation of the PV-powered fan. The table below lists the interior temperature and glycerol temperature for different ambient conditions 03.06.2012. FIG. 5 represents the temperature profile graph with operation of fan in SPTR-1 (B) and at the ambient temperature (A), as obtained from Table 2.

TABLE 2

Control Temperature profile using dc fan

| Time | Temperature obtained | Ambient temperature |
|---|---|---|
| 11.30 | 47.3 | 37 |
| 11.45 | 58 | 38 |
| 12.00 | 57 | 39 |
| 12.15 | 63 | 38 |
| 12.30 | 63 | 41 |
| 12.45 | 62 | 41 |
| 13.00 | 62 | 40 |
| 13.15 | 59 | 39 |
| 13.30 | 58 | 38 |
| 13.45 | 58 | 38 |

Example 3

Benzylic Bromination in SPTR 1

Bromination reactions were conducted in the device of Example 1 under stirring and with or without operation of the fan. Initially reactions were conducted with p-nitrotoluene as per the equation below. The reactions were carried out without the use of any organic solvents. The table shows that the reactions could be carried out cleanly and efficiently in the unit. It can also be seen that the temperature could be controlled in the range of 55° C.-65° C.

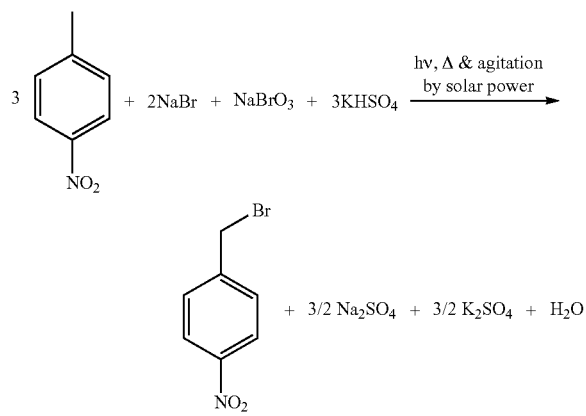

In the same way p nitro benzyl bromide was synthesized from p-nitrotolune reaction temperature continued to rise to ca. 90° C. and then remained almost constant. The reaction was continued for 2.5 h and the GC yield on reagent basis was found to be 93%. When the same reaction was repeated with operation of the PV-powered fan, the average temperature of the reaction dropped to 65° C. as a result of convective heat loss, while the GC yield rose to 95%. When the RB flask was blackened to prevent exposure of the contents to light, the yield observed was only 19%.

TABLE 3

Bromination of PNT in SPTR 1

| Entry | PNT g/mmol | Br mmol | Temp. control through fan | Average reaction T/° C. | hv | Reaction time/h | GC yield on Br basis/% |
|---|---|---|---|---|---|---|---|
| 1 | 10/73 | 24.5 | No | 88 | Yes | 2.5 | 93 |
| 2 | " | " | Yes | 65 | Yes | 2.2 | 95 |
| 3 | " | " | Yes | 65 | No | 2.5 | 19 |

Example 4

Figure 6:
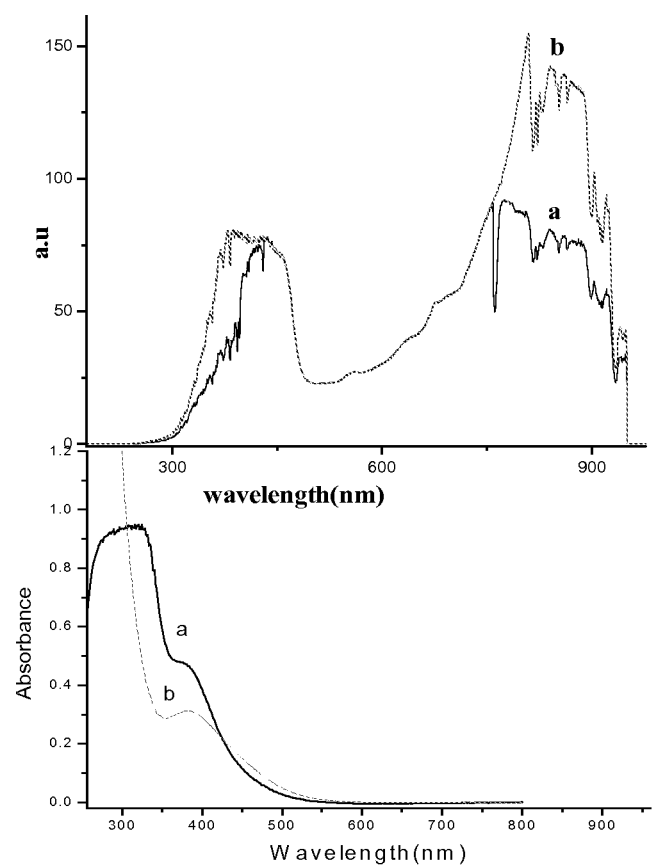
FIG. 6 represents top (A) relative intensity of solar radiation through SPTR 1, (B) relative intensity of solar radiation on horizontal, (C) relative intensity of tungsten lamp. Bottom (A) UV-Vis absorption spectra profile of $Br_2$, (B) UV-Vis absorption spectra profile of reaction mixture.

FIG. 6(A) shows the spectral profiles, along with relative intensities, of the global insolation and solar illumination as measured inside the SPTR1. The latter was nearly two-fold higher. FIG. 6(B) shows the absorption spectrum of the active brominating agent generated upon addition of a small amount of $KHSO_4$ (10-20% of stoichiometric requirement) into an aqueous solution of 2:1 $Br^-$—$BrO_3^-$. The shoulder at 392 nm matched well with that of aqueous $Br_2$. Thus the bromine generated in small amounts in the aqueous solution of active brominating agent was the photoactive species yielding Br radical.

Example 5

Other benzylic bromination reaction were carried out in SPTR1:

TABLE 4

Bromination of toluene derivatives:

| Entry | Substrate | gm/mmol | Desired Product | Time min | Average reaction temp.(oC) | Conversion by GCa (%) |
|---|---|---|---|---|---|---|
| 1 | 4-Cl-toluene | 1.14/9.0 | 4-Cl-benzyl bromide | 120 | 58 | 98 |
| 2 | 4-Br-toluene | 1.59/9.3 | 4-Br-benzyl bromide | 135 | 72 | 97 |
| 3 | 3-NO2-toluene | 11.17/81.5 | 3-NO2-benzyl bromide | 110 | 63 | 98 |

TABLE 4-continued

Bromination of toluene derivatives:

| Entry | Substrate | gm/mmol | Desired Product | Time min | Average reaction temp.(oC) | Conversion by GCa (%) |
|---|---|---|---|---|---|---|
| 4 | 4-fluorotoluene | 0.99/9.0 | 1-(bromomethyl)-4-fluorobenzene | 40 | 72 | 97 |
| 5 | toluene | 4.71/51.1 | benzyl bromide | 90 | 57 | 99 |
| 6 | ethylbenzene | 1.93/18.2 | (1-bromoethyl)benzene | 50 | 72 | 87 |
| 7 | n-propylbenzene | 1.09/9.1 | (1-bromopropyl)benzene | 90 | 55 | 88 |

Example 6

Bromination reaction of some linear chain hydrocarbon like n-hexane, n-heptane and n-pentane, cyclic hydrocarbon like cyclohexane, cycloheptane, cyclooctane, cyclodecane and norbornane were also carried out in SPTR1:

TABLE 5

Bromination of cyclic alkanes and linear alkanes:

| Entry | Substrate | Time min(h) | Average reaction temp.(oC) | product/yield[a] |
|---|---|---|---|---|
| 1 | n-hexane | 1.5 | 57 | 3-bromohexane 46% / 2-bromohexane 31% |
| 2 | n-heptane | 1.0 | 55 | 3-bromoheptane 72% / 2-bromoheptane 19% |

TABLE 5-continued

Bromination of cyclic alkanes and linear alkanes:

| Entry | Substrate | Time min(h) | Average reaction temp.(oC) | product/yield[a] |
|---|---|---|---|---|
| 3 | cycloheptane | 1.0 | 61 | bromocycloheptane 82% |
| 4 | cyclooctane | 1.5 | 60 | bromocyclooctane 87% |
| 5 | norbornane | 1.5 | 63 | bromonorbornane 78% |
| 6 | cyclodecane | 2.0 | 67 | bromocyclodecane 67%[b] |

[a] indicated isolated yield except entry 6.
[b] indicated GC yield

Example 7

4-Bromo-2,5-disubstituted oxazoles were synthesized from the corresponding N-phenylethylamides via successive benzylic bromination with NBS. The reactions were conducted in a solar photo-thermochemical reactor gave 63-79% isolated yield with EDC as solvent in short span of reaction time.

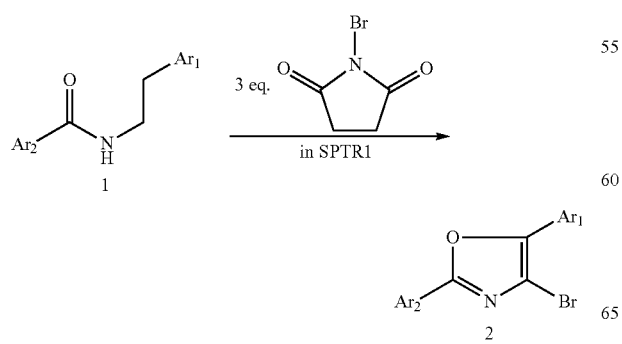

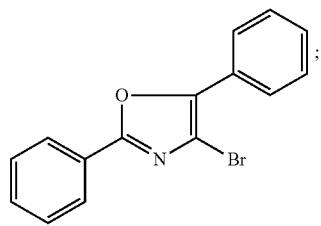

2a

73%

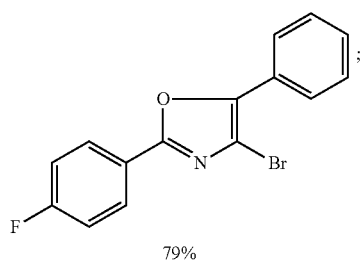

2b

79%

-continued

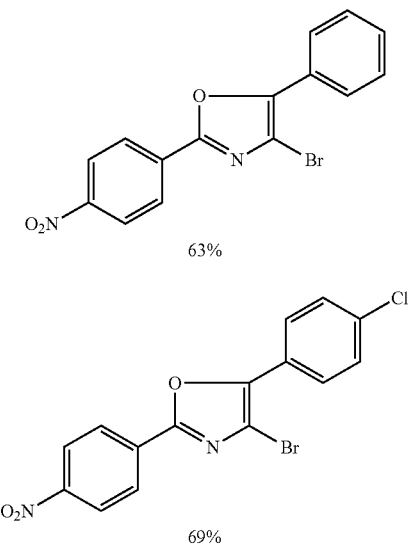

2c

63%

2d

69%

ADVANTAGES OF THE INVENTION

1. The present invention is a standalone device useful for undertaking organic reactions utilizing solar power alone whether it be it for heat and/or light and/or agitation.
2. The invention can be used for bromination at $sp^3$ carbon speedily with high efficiency.
3. The invention promotes popularization of solar energy use in chemical reactions by making such a device compact and easy-to-maintain and further making it available at affordable cost.

We claim:

1. A laboratory scale solar photo thermo-chemical reactor unit comprising:
   a cooker type black painted box;
   a solar Photovoltaic (PV) panel attached to an angle assembly comprising a plurality of V-trough reflectors on north-south edges,
   wherein the PV panel is positioned over the cooker type black painted box;
   wherein the cooker type black box comprises:
   a lid assembly,
   a photovoltaic (PV) operated direct current (DC) fan fitted onto one side of the box,
   an air outlet configured to control temperature on the other side, and
   a PV operated magnetic stirrer positioned at a base of the box, and wherein the unit comprises wheels configured to enable mobility of the entire unit.

2. The unit as claimed in claim 1, wherein the unit further comprises a round bottom flask of up to 500 mL capacity.

3. The unit as claimed in claim 1, wherein an angle of the plurality of V-trough reflectors on north-south edges is adjusted to attain a maximum solar radiation on the lid assembly such that a maximum temperature of 109° C. of a liquid in a flask is attained.

4. The unit as claimed in claim 1, wherein the photovoltaic (PV) operated DC fan and the air outlet controls temperature of reaction in a liquid in a flask in the range of 50-70° C.

5. The unit as claimed in claim 3, wherein the angle of the plurality of V-trough reflectors on north-south edges is adjusted to attain solar radiation in the wavelength range of 300-900 nm.

6. The unit as claimed in claim 1, wherein the PV panel has a power rating of 20 W.

7. A process for conducting photo-thermochemically activated and agitation-promoted organic reactions in the unit of claim 1, wherein thermal energy, illuminance and mechanical energy for agitation are all derived simultaneously from incident solar radiation.

8. The process as claimed in claim 7, wherein the reactions are conducted with up to 250 g of substrate.

9. The process as claimed in claim 7, wherein the organic reactions conducted comprise benzylic bromination and reactions thereof.

10. The process as claimed in claim 7, wherein the organic reactions conducted comprise bromination of alkanes.

11. The unit of claim 3, wherein the liquid is glycerol.

12. The process of claim 9, wherein said organic reactions comprise oxazole ring formation.

* * * * *